United States Patent [19]
Weinstein et al.

[11] Patent Number: 5,830,490
[45] Date of Patent: Nov. 3, 1998

[54] METHOD AND DEVICE FOR ORGANIZING AND COORDINATING THE COMBINED USE OF TOPICAL AEROSOLS AND ORAL MEDICATIONS FOR THE TREATMENT OF DISORDERS

[76] Inventors: Robert E. Weinstein, Boston, Mass.; Alan M. Weinstein, Potomac, Md.

[21] Appl. No.: 825,999

[22] Filed: Apr. 4, 1997

[51] Int. Cl.$^6$ .................................. A61L 9/04; A61K 7/04
[52] U.S. Cl. ..................... 424/405; 424/400; 424/439; 424/451; 424/464; 424/10.1; 424/10.2; 514/826; 514/853; 514/885; 514/929; 514/958; 206/534; 206/538; 206/828
[58] Field of Search ..................... 206/828, 534, 206/538; 424/400, 45, 439, 451, 464, 489, 10.1, 10.2, 10.3; 514/826, 853, 885, 969, 958

[56] References Cited

U.S. PATENT DOCUMENTS

| | | | |
|---|---|---|---|
| 4,039,080 | 8/1977 | Cappuccilli | 206/534 |
| 4,295,567 | 10/1981 | Knudsen | 206/534 |
| 4,553,670 | 11/1985 | Collens | 206/534 |
| 4,593,819 | 6/1986 | Will | 206/538 |
| 4,736,849 | 4/1988 | Leonard et al. | 206/534 |
| 4,828,113 | 5/1989 | Friedland et al. | 206/570 |
| 5,002,048 | 3/1991 | Makiej, Jr. | 128/200.23 |
| 5,007,419 | 4/1991 | Weinstein et al. | 128/200.23 |
| 5,181,189 | 1/1993 | Hafner | 368/10 |
| 5,377,841 | 1/1995 | Varon | 206/570 |
| 5,437,267 | 8/1995 | Weinstein et al. | 128/200.23 |
| 5,489,026 | 2/1996 | D'Aloia | 206/570 |
| 5,489,027 | 2/1996 | Goerigk | 206/570 |

OTHER PUBLICATIONS

Leape, et al., "Systems Analysis of Adverse Drug Events", *JAMA*, Jul. 5, 1995, vol. 274, No. 1, pp. 35–43.
Knox, Richard A., "Hospital Drugs Hurt 1 in 15", *The Boston Globe*, Jul. 5, 1995, vol. 248, No. 5, pp. 1 and 13.
Guest Editorial, "Building Partnerships with Patients", *Annals of Allergy, Asthma & Immunology*, Jan., 1997, vol. 78, pp. 1 & 4.
Kelloway, et al., "Comparison of Patients' Compliance with Prescribe Oral and Inhaled Asthma Medications", *Arch Intern Med.*, Jun. 27, 1997, vol. 154, pp. 1349–1352.

*Primary Examiner*—Neil S. Levy
*Attorney, Agent, or Firm*—Hopgood, Calimafde, Kalil & Judlowe

[57] ABSTRACT

A method and device for organizing, storing, instructing, and coordinating the combined use of aerosol and oral medications for the treatment of disorders including respiratory tract disorders for the purpose of reducing medication error and increasing therapeutic compliance.

9 Claims, 2 Drawing Sheets

METHOD AND DEVICE FOR ORGANIZING AND COORDINATING THE COMBINED USE OF TOPICAL AEROSOLS AND ORAL MEDICATIONS FOR THE TREATMENT OF DISORDERS

BACKGROUND OF THE INVENTION

1. Field of Invention

The present invention relates to a method and device for organizing, storing, and coordinating the combined use of aerosol and oral medications for the treatment of disorders including respiratory tract disorders for the purpose of reducing medication error and increasing therapeutic compliance.

2. Technical Review

Many drugs are utilized by patients over a period of time in varying amounts and in varying order to provide for their effective administration. Packaging has been developed for aiding the user of such drugs to comply with the proper administration over the proper time period. The dispensing apparatus associated with such multiple day administrative drugs are typically directed to the administration of pills or capsules, or similar solid medication.

U.S. Pat. No. 4,039,080, for example, discloses a tray having individual compartments for pills which may contain a week's medication with indicia indicating the day of the week and time of the day the medication is to be taken.

U.S. Pat. No. 4,553,670 discloses another device comprising a support on which are located two different ingestible medicinal substances in a single dose form with an adjacent portion for instructional information.

U.S. Pat. No. 4,593,819 discloses a covered pill tray of rectangular configuration having an array of open-topped compartments to hold a supply of medication arranged by the day and time of taking the medication.

U.S. Pat. No. 4,736,849 discloses a method and another type of dispenser for the storage and dispensing of calendar-oriented pills. U.S. Pat. No. 5,181,189 discloses a device for storage and time-regulated dispensing of drugs which includes a drug container to which is secured a signal generator.

U.S. Pat. No. 5,377,841 discloses a sleep therapy package which includes an audio recording of program material for inducing sleep, a card having a plurality of doses, some of which are medicine for inducing sleep and at least one of which is a placebo, along with patient instructions.

Cartonless packaging systems for containing liquids used, for example, as ophthalmic products, which also contain means for storing tablets and instructional material are disclosed in U.S. Pat. Nos. 5,489,026 and 5,489,027.

While the marketplace abounds with pill boxes and organizers for oral medications, no such organization tool is presently available for a lay person to organize aerosols together with oral medications. Further, no pharmaceutically formulated device which combines aerosol and oral therapeutic modalities together into a single organized treatment device with clear indicia and coordinated instructions is presently commercially marketed.

There is a need for a device which combines topical (aerosol) and systemic (oral) modalities for treatment of diseases such as, for example, respiratory disorders. There is further a need for a method of reducing medication error and for enhancing therapeutic compliance of combined topical/systemic modality therapeutic regimens. It is therefore the object of the present invention to provide these devices and methods.

SUMMARY OF THE INVENTION

In accordance with the foregoing objectives, the present invention comprises a device for reducing medication error and enhancing therapeutic compliance of combined aerosol and systemic modalities for treatment of disorders, such as respiratory disorders, comprising: (a) at least one topical multi-dosage aerosol medication (b) at least one oral medication (c) indicia for distinguishing the medications (d) instructions for coordination of the medications use together as a single therapeutic regimen and (e) a unifying container. The present invention further comprises a method of reducing medication error and enhancing therapeutic compliance of combined topical and systemic treatments of disorders, such as respiratory disorders, comprising the step of: utilizing a combined aerosol and oral therapeutic regimen contained within such a unified device.

DETAILED DESCRIPTION OF THE PREFERRED EMBODIMENT

Figure 1:
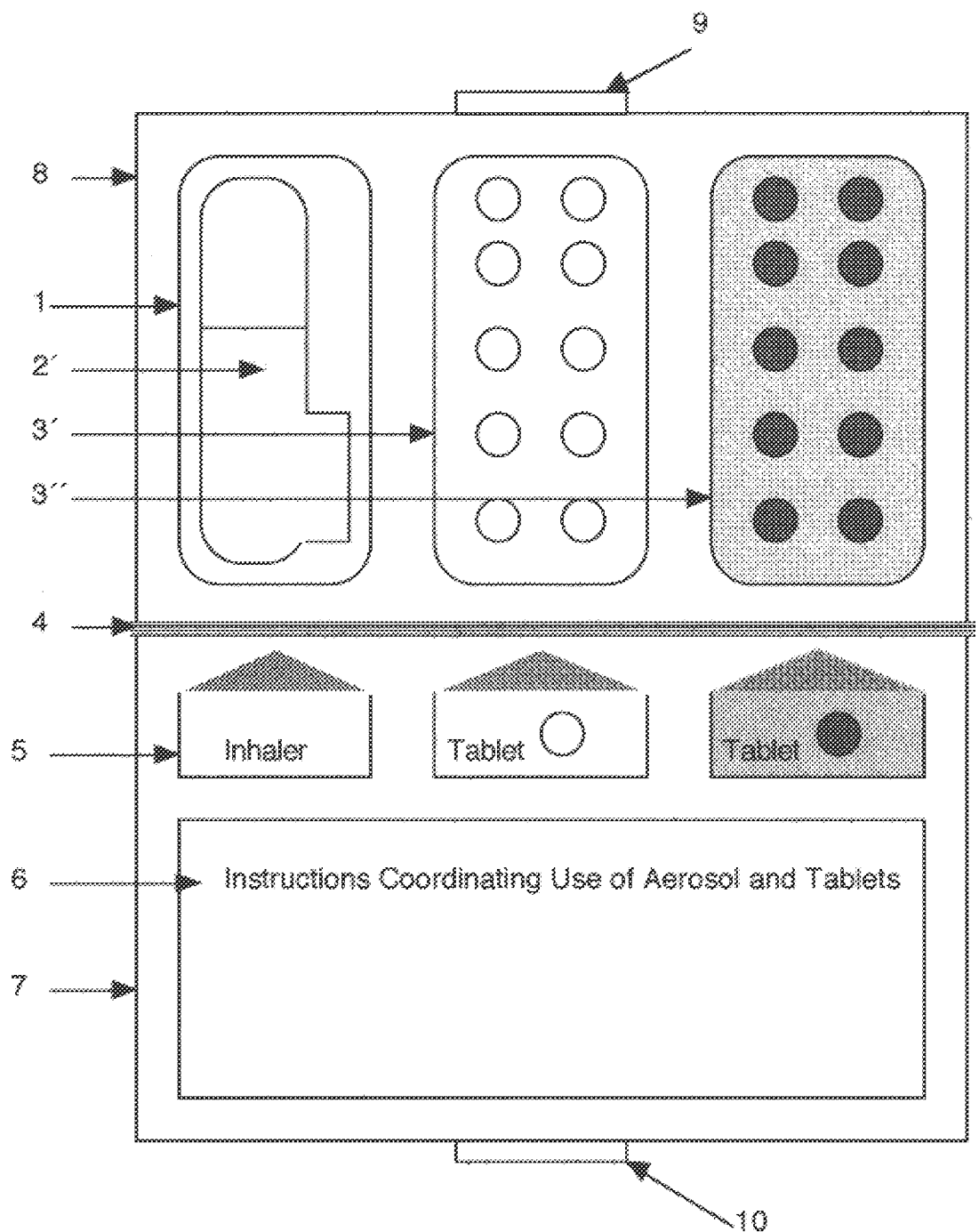
FIG. 1 is a plan view of a container in accordance with the present invention.

The following detailed description of the invention is provided to aid those skilled in the art in practicing the present invention. However, it should not be construed to unduly limit the present invention. Variations and modifications in the disclosed embodiments may be made by those of ordinary skill in the art without departing from the scope of the present inventive discovery.

The present invention provides a unifying dispensing container for medicaments for treatment of disorders requiring a combined topical and systemic regimen and a method for reducing medication error and enhancing therapeutic compliance of combined topical and systemic modalities for treatment of such disorders. The unifying container holds at least one topical multi-dosage unit aerosol medication and at least one oral medication, indica for distinguishing these medications, and instructions for their coordinated use together as a single therapeutic regimen. It is to be understood that by multi-dosage aerosol unit it is meant that more than one dosage unit is available within the aerosol medication. The oral medication may be in the form of a tablet, pill, capsule, caplet, packets or containers of liquids, gels, or solids, some of which may require reconstituting, or any generally recognized oral form of medication.

Referring to the drawings, it will be understood that while preferred embodiments of the invention have been illustrated and described, the invention is not limited to such embodiments. Changes and additions may be made therein and thereto without departing from the spirit of the invention.

Figure 2:
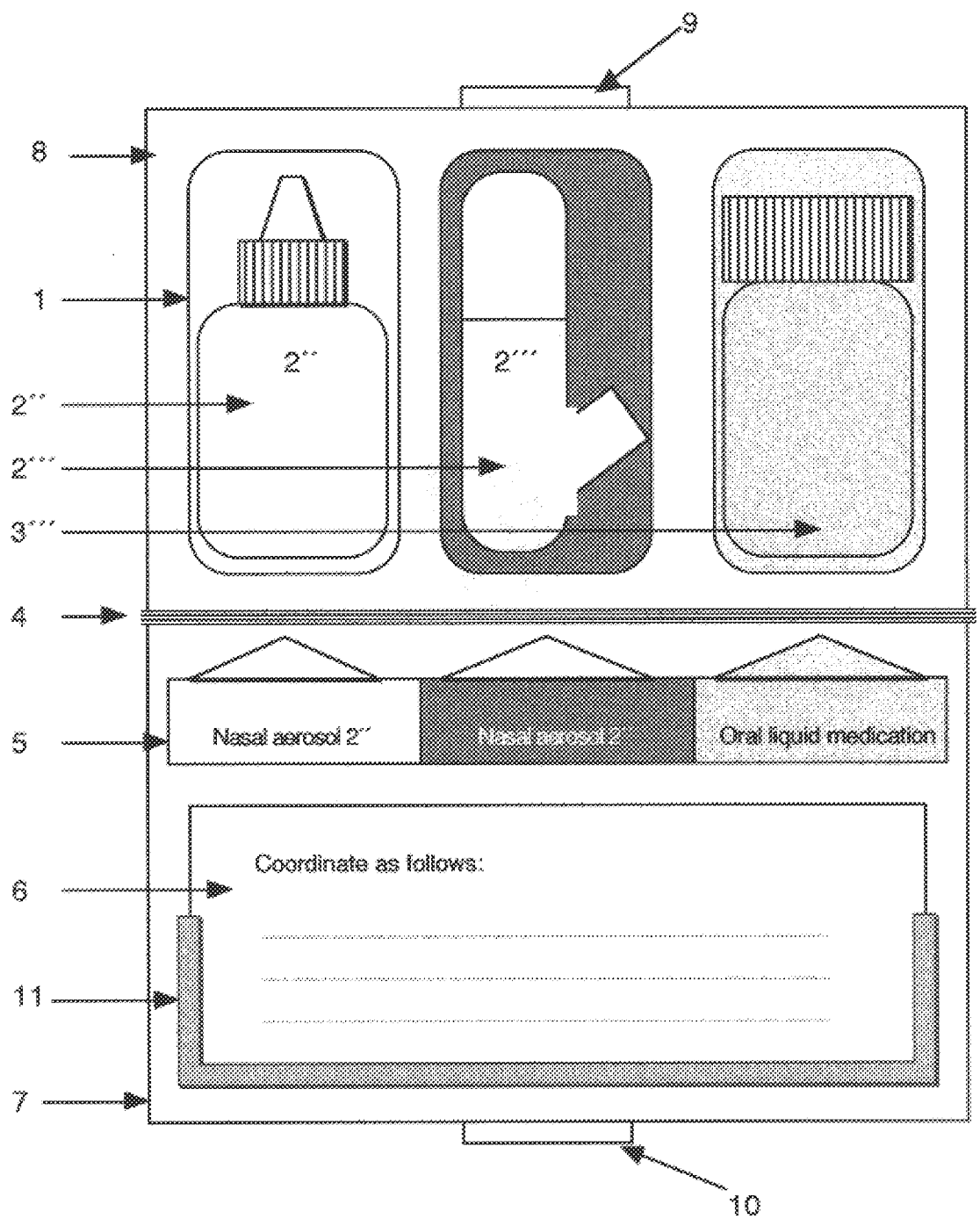
FIG. 2 is a plan view of another container in accordance with the present invention.

Two embodiments of the unifying container of the present invention are depicted in FIG. 1 and FIG. 2. Referring to FIG. 1, a support package 1 which houses an aerosol 2' and oral medication in the form of tablets in a blister wrap 3' and 3" is illustrated. The technique of making and attaching such wraps is well known and will not therefore be further described. A fold 4 in the package is provided in the center. Identifying indicia 5 is provided directly under and aligned with each respective aerosol and tablet or oral medication housing. An instruction bearing portion 6 provides instructions coordinating use of the aerosol and oral medication.

The instructions are either unalterable or capable of being altered yet maintained within the unifying container. FIG. 2 shows a frame 11 to accommodate interchangeable instructions. The instruction bearing portion may also include an erasable pad or a pad with multiple blank tear off sheets. The lid portion 7 and the bottom portion 8 of the support package each contain respective clasp portions 9 and 10 which can be secured together when the support package is folded along fold 4. FIG. 2 depicts an embodiment which contains two different aerosols 2'' and 2''' and one oral medication in liquid form 3'''.

Although the embodiments specifically described herein have either one aerosol and two oral medicament housings, or two aerosol and one oral medicament housings, packaging containing other numbers of multiple aerosol and multiple oral medicament housings are also within the scope of this invention. The packaging may be adapted in accordance with the requirements of the regimen by widening the packaging and increasing the number of blister housings and indicia. Additionally, the packaging may be in any geometric configuration and the containers are not limited to blister packs. Any pharmaceutical container may be suitable.

Treatment for disorders which necessitate a multiplicity of components may pose a number of problems for some patients. These multiple medication treatments may be a source of confusion and frustration which can result in medication error or lack of compliance. For example, the individual components may be lost, misplaced, or ignored. The least used, least immediate acting, or least obvious acting components, even if important, are the ones most likely to be lost or ignored. The most usual problem associated with this type of treatment is the lack of coordinating indicia and instructions being readily available to the patient for verifying the multiple components use together.

These problems are apparent to most practicing health care providers. Many patients who are confronted with a multiplicity of aerosols and oral medications get confused and lose track of which medication is which. Many patients also lose instructions issued separate from the medication, and/or use the most rapidly acting medication and abandon the medication offering less immediate action albeit offering enhanced long-term effect. Furthermore, in spite of careful oral and written instruction from the health care provider, many patients are known to use what they have conveniently available. These haphazard applications of medications can result in treatment failure. In addition, it results in further expense for the patient who eventually will have to seek additional professional medication consultation involving additional medical personnel time and expense to instruct and organize therapy for these individuals. The devices and methods of the present invention would greatly help overcome these noted problems.

Additionally, cost factors, as well as outcomes, are now being carefully considered by medical groups. There is a definite need for devices and methods which would help patients be more cognizant of their proper medication treatment and therapy regiments. Such devices and methods would improve and ensure patient compliance. They would provide not only a means of further instruction but also provide an organizational tool which can save additional medical personnel expenditures. Successful therapy is less costly than unsuccessful treatment which eventuates in prolonged illness, multiple illnesses, multiple clinic visits, or hospitalizations.

One disease, for example, wherein a multiplicity of medications are utilized in treatment is respiratory tract disorders. Because the respiratory mucosa is structured as a conduit for air, it is possible to deliver medication topically to the respiratory mucosa by aerosol. It is also possible to deliver medication which reaches the respiratory tract via systemic absorption by oral administration. Often it is advisable for individuals suffering from respiratory tract disorders such as rhinitis, bronchitis, or asthma to utilize both routes for the treatment of respiratory disorders, i.e., a combination of aerosol (topical) and oral (systemic) medication as a treatment regime.

Topical aerosol medications which are presently in use for the treatment of rhinitis include: corticosteroids, which reduce inflammation of the nasal mucous membranes decongestants, which constrict the nasal mucous membranes cell stabilizers, which inhibit the release of symptom-causing mediators, antihistamines which block the mediator histamine after it has been released in the inflammatory process, and anticholinergic agents which dry nasal mucous membranes.

Oral medications which are currently used for the treatment of rhinitis include corticosteroids, decongestants, antihistamines which block the mediator histamine after it has been released in the inflammatory process, and antibiotics in the instance of complicating infections.

Topical aerosol medications which are currently used for the treatment of bronchial disorders such as bronchitis and asthma include: corticosteroids, which reduce inflammation of the bronchial mucous membranes, adrenergic agonists, which relax bronchial smooth muscle, cell stabilizers, which inhibit the release of symptom-causing mediators, and anticholinergic agents which open and dry the bronchial tree.

Oral medications which are currently used for the treatment of bronchial disorders such as bronchitis and asthma include: corticosteroids, adrenergic agonists (bronchodilators), which relax bronchial smooth muscle, xanthene derivatives which also reverse bronchial smooth muscle spasm, mediator inhibitors such as zafirlukast which antagonizes the action of leukotrienes, and antibiotics in the instance of infection such as bronchitis.

One embodiment of the present invention consists of both inhalational medication(s) for the treatment of respiratory tract disorders and oral medication(s). Both are contained within a container, which in a preferred embodiment, accommodate both in an easily visible and compact manner, along with indicia for each medicament component and instructions for the coordination of the medications together into a single therapeutic regimen.

The choice of medications and their use together is dependent on numerous considerations besides mechanism of action and risks of the individual medications, and include absorption, time of onset after dosing, rate of elimination, duration of action after dosing, therapeutic effect by virtue of combination, and side effects by virtue of combination. Medication error and misuse due to a multiplicity of medications and modalities pose an additional risk. Medical/pharmaceutical expertise is clearly required to formulate a treatment regime utilizing a combination of topical and systemic medications and appropriate instructions for use by a lay individual affected by respiratory disorder.

EXAMPLES

The invention will be further clarified by a consideration of the following examples, which are intended to be purely exemplary of the invention.

Example 1

Topical Intranasal Aerosol Medication(s) and Oral Medication(s) for the Treatment of Rhinitis.

One beneficial treatment regime method for rhinitis might include the use of a topical intranasal corticosteroid to reduce inflammation and an oral antihistamine to block the action of released histamine. Medications exemplifying this regimen might be: Beconase Nasal Spray® (beclomethasone diprionate) (anti-inflammatory corticosteroid) one spray in each nostril four times a day and Nolahist Tablets® (phenindamine tartrate) (an antihistamine) one 25 mg tablet four times a day.

Example 2

Topical Intranasal Aerosols and Oral Medication Regimen for the Treatment of Rhinitis.

Another beneficial treatment regime might include a topical intranasal decongestant, a topical intranasal corticosteroid and a liquid oral antihistamine. Topical intranasal decongestants are generally rapidly acting and may bring about immediate relief but may cause irritation over time. Topical intranasal corticosteroid generally act more slowly over days to weeks but tend to bring about more permanent relief. The use of the two topical agents, with decongestant first, and corticosteroid following is the preferable order of use, since the decongestant can improve nasal patency rapidly and allow the corticosteroid improved passage into the nose. Both aerosol units might be combined with an antihistamine in liquid form. Because relief immediately follows topical intranasal decongestant use, individuals might be included to ignore the use of the remainder of the regimen if they were not linked by package and instruction, with a resulting negative effect: rebound, overuse of decongestant, irritation and inflammation, a common outcome of the use of topical decongestant alone.

Medications exemplifying this regimen might be: Neo-Synepherine Nasal Spray® (phenyleprine hydrochloride) (decongestant) two sprays in each nostril four times a day followed by Beconase Nasal Spray® (beclomethasone diprionate) one spray in each nostril four times a day and Nolahist Tablets® (phenindamine tartrate) one 25 mg tablet four times a day.

Example 3

Topical Bronchial Aerosol Medication and Oral Medication(s) for the Treatment of Bronchial Respiratory Disorders.

One beneficial treatment regime for bronchial respiratory disorders might include the use of a topical inhaled corticosteroid to reduce inflammation and an oral adrenergic agonist to reduce bronchial smooth muscle constriction. The oral medication is preferably taken after the aerosol resulting in removal of topical corticosteroid which has deposited in the mouth and pharynx. This necessary deposit of medication serves no beneficial action for the bronchial disorder, but may lead to increased unwanted topical absorption or to local fungal overgrowth. If washed away from these areas in the process of swallowing oral medication, this residual corticosteroid may be inactivated in the stomach. Oral medication may be in the form of a tablet, pill, capsule, caplet, packets or containers of liquid, gel, or solid, some of which may require reconstituting, or any generally recognized oral form of medication.

Medications exemplifying this regimen might be: Becolvent Inhalational Aerosol (beclomethasone, USP) (corticosteroid) two sprays inhaled four times a day followed by Proventil Tablets, 2 mgm. (Albuteral Sulfate) (bronchodilator) four times a day with water.

Example 4

Topical Bronchial Aerosol-Oral Medications Regimen for the Treatment of Bronchial Respiratory Disorders.

Another treatment regime might include a topical inhaled rapidly acting adrenergic agonist, a topical inhaled corticosteroid, and oral theophylline, each having a separate mechanism of action. A preferred order of administration would be: (1) inhaled adrenergic agent first to provide rapid smooth muscle relaxation and bronchial dilatation, (2) allowing improved distribution of the inhaled corticosteroid, and lastly, (3) the oral medication to further open the airways, albeit more slowly, and for the liquids taken to swallow the medication to wash away oral and pharyngeal deposits of corticosteroid. This combination of medication has been commonly utilized and it is not uncommon for the more immediate acting medication, the inhaled adrenergic agent, to be most used and the others ignored, although compliance with this regimen is more likely to bring about settling of inflammation and more prolonged relief. Keeping the components of the treatment regime together and physically organized with indicia and combined instructions provides convenience and organization, and promotes compliance with the treatment regimen with less confusion, treatment errors and improved outcomes. Medications for this regimen may include: Ventolin Inhalation Aerosol® (albuterol, USP) (bronchodilator) inhale two sprays four times a day Beclovent Inhalational Aerosol® (belcomethasone, USP) (corticosteroid) inhale two sprays four times a day and Quibron®-T (theophylline tablets, USP) (an oral bronchodilator-different mechanism of action than Ventolin) one 300 mg tablet four times a day.

Example 5

Topical Medication(s) and Oral Medication(s) for the Treatment of Rhinitis and Bronchial Respiratory Disorders.

Upper respiratory (nasal) and lower respiratory (bronchial) disorders frequently occur together. It is well established that bronchial disorders may not improve unless concomitant nasal disorders are adequately treated. For example, nasal polyps with consequent sinus congestion may coexist with asthma and perpetuate asthmatic symptoms. For this reason, a combination of topical and oral medications may be indicated for rhinitis with nasal polyps and bronchial respiratory disorders. Such a combination might include nasal and bronchial aerosol devices and oral medications. Medication for the regimen may include: Beconase Nasal Spray® (beclomethasone diprionate) (corticosteroid) one spray in each nostril four times a day, Ventolin Inhalation Aerosol® (albuterol, USP) (bronchodilator) inhale two sprays four times a day, followed by Beclovent Inhalational Aerosol® (beclomethasone, USP) (corticosteroid) inhale two sprays four times a day, followed by Nolahist Tablets® (phenindamine tartrate) (antihistamine) one 25 mg tablet four times a day, and Quibron®-T (theophylline tablets, USP) (bronchodilator, xanthene derivative) one 300 mg tablet four times a day.

Other variations may occur to those skilled in the art which are within the scope of the invention as set forth in the appended claims. Those of skill in the art may also recognize modifications to these presently disclosed embodiments. These variations and modifications are meant to be covered by the spirit and scope of the present claims.

What is claimed is:

1. A therapeutic system for reducing medication error and enhancing therapeutic compliance of combined topical and systemic treatments, comprising:

a dispenser for housing (a) at least one medication administered topically to the respiratory tract and present in a multi-dosage container;

(b) multiple dosages of at least one oral medication;

(c) indicia operably associated with said dispenser for distinguishing the topical and oral medications from each other; and (d) instructions operably associated with said dispenser for coordinating administration of the topical and oral medications for use as a therapeutic regimen, wherein the topical medication is selected from the group consisting of corticosteroids, decongestants, cell stabilizers, bronchodilating adrenergic agonists, antihistamines, and anticholinergic agents; and the oral medication is selected from the group consisting of corticosteroids, decongestants, antihistamines, bronchodilating adrenergic agonists, xanthene derivatives, mediator antagonists, and antibiotics.

2. The device of claim 1 wherein the oral medication is in the form of a tablet, pill, capsule, caplet, liquid, powder or gel.

3. A method of reducing medication error and enhancing therapeutic compliance of combined topical and systemic treatments effective for treating a respiratory condition selected from the group consisting of rhinitis, bronchitis, and asthma, comprising the steps of:

providing a combined aerosol and oral therapeutic regimen contained within a unified device in which is provided:

(a) at least one first medication in a form suitable for topical administration to the respiratory tract and in an amount sufficient for multiple dosages;

(b) multiple dosages of at least one second oral medication;

(c) indicia for distinguishing the first and second medications; and (d) instructions for coordinating the use of the topical and oral medications as a therapeutic regimen, wherein the topical medication is selected from the group consisting of corticosteroids, decongestants, cell stabilizers, bronchodilating adrenergic agonists, antihistamines, and anticholinergic agents; and the oral medication is selected from the group consisting of corticosteroids, decongestants, antihistamines, bronchodilating adrenergic agonists, xanthene derivatives, mediator antagonists and antibiotics and administering said topical medication and said oral medication according to said instructions.

4. A therapeutic system for reducing medication error and enhancing therapeutic compliance of combined topical and systemic treatments effective for treating the respiratory disorder rhinitis, comprising:

a dispenser for housing (a) at least one first medication administered topically to the nasal passages and present in a multi-dosage container;

(b) multiple dosages of at least one second oral medication;

(c) indicia operably associated with said dispenser for distinguishing the first and second medications from each other; and (d) instructions operably associated with said dispenser for coordinating administration of the first and second medications as a therapeutic regimen, wherein the topically administered medication is selected from the group consisting of corticosteroids, decongestants, cell stabilizers, antihistamines, and anticholinergic agents; and the oral medication is selected from the group consisting of corticosteroids, decongestants, antihistamines, mediator antagonists, and antibiotics.

5. A method of reducing medication error and enhancing therapeutic compliance of combined topical and systemic treatments effective for treating the respiratory condition rhinitis, comprising the steps of:

providing a combined aerosol and oral therapeutic regimen contained within a unified device in which is provided:

(a) at least one first medication in a form suitable for topical administration to the nasal passages and in an amount sufficient for multiple dosages and selected from the group consisting of corticosteroids, decongestants, cell stabilizers, antihistamines, and anticholinergic agents;

(b) multiple dosages of at least one second oral medication selected from the group consisting of corticosteroids, decongestants, antihistamines, mediator antagonists, and antibiotics;

(c) indicia for distinguishing the first and second medications; and (d) instructions for coordinating use of the topical and oral medications as a therapeutic regimen; and administering said topical medication and said oral medication according to said instructions.

6. A therapeutic system for reducing medication error and enhancing therapeutic compliance of combined topical and systemic treatments effective for treating a respiratory disorder selected from the group consisting of bronchitis and asthma, comprising:

a dispenser for housing (a) at least one first medication administered topically to the respiratory tract and present in a multi-dosage container;

(b) multiple dosages of at least one second oral medication;

(c) indicia operably associated with said dispenser for distinguishing the first and second medications from each other; and (d) instructions operably associated with said dispenser for coordinating administration of the first and second medications as a therapeutic regimen, wherein the topically administered medication is selected from the group consisting of corticosteroids, decongestants, cell stabilizers, bronchodilating adrenergic agonists, antihistamines, and anticholinergic agents; and the oral medication is selected from the group consisting of corticosteroids, decongestants, antihistamines, bronchodilating adrenergic agonists, xanthene derivatives, mediator antagonists, and antibiotics.

7. A method of reducing medication error and enhancing therapeutic compliance of combined topical and systemic treatments effective for treating a respiratory condition selected from the group consisting of bronchitis and asthma, comprising the steps of:

providing a combined aerosol and oral therapeutic regimen contained within a unified device in which is provided:

(a) at least one first medication in a form suitable for topical administration to the respiratory tract and in an amount sufficient for multiple dosages and selected from the group consisting of corticosteroids, decongestants, cell stabilizers, bronchodilating adrenergic agonists, antihistamines, and anticholinergic agents;

(b) multiple dosages of at least one second oral medication selected from the group consisting of corticosteroids, decongestants, antihistamines, bronchodilating adrenergic agonists, xanthene derivatives, mediator antagonists, and antibiotics;

(c) indicia for distinguishing the first and second medications; and (d) instructions for coordinating use of the topical and oral medications as a therapeutic regimen; and administering said topical medication and said oral medication according to said instructions.

8. A therapeutic system for reducing medication error and enhancing therapeutic compliance of combined topical and systemic treatments effective for treating a respiratory disorder selected from the group consisting of rhinitis, bronchitis, and asthma, comprising:

a dispenser for housing (a) at least one medication administered topically to the respiratory tract and present in a multi-dosage container;

(b) multiple dosages of at least one oral medication;

(c) indicia operably associated with said dispenser for distinguishing the topical and oral medications from each other; and (d) instructions operably associated with said dispenser for coordinating administration of the topical and oral medications as a therapeutic regimen wherein the topical medication is selected from the group consisting of corticosteroids, decongestants, cell stabilizers, bronchodilating adrenergic agonists, antihistamines, and anticholinergic agent and the oral medication is selected from the group consisting of corticosteroids, decongestants antihistamines, bronchodilating adrenergic agonists xanthene derivatives mediator antagonists and antibiotics.

9. The device of claim 8 wherein the oral medication is in the form of a tablet, pill, capsule, caplet, liquid, powder, or gel.

* * * * *